United States Patent
Govari et al.

(10) Patent No.: US 10,751,121 B2
(45) Date of Patent: Aug. 25, 2020

(54) ULTRASOUND TRANSDUCERS ON PREDETERMINED RADII OF BALLOON CATHETER

(71) Applicant: Biosense Webster (Israel) Ltd., Yokneam (IL)

(72) Inventors: Assaf Govari, Haifa (IL); Christopher Thomas Beeckler, Brea, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 190 days.

(21) Appl. No.: 15/637,191

(22) Filed: Jun. 29, 2017

(65) Prior Publication Data

US 2019/0000544 A1    Jan. 3, 2019

(51) Int. Cl.
| | |
|---|---|
| *A61B 18/14* | (2006.01) |
| *A61B 8/12* | (2006.01) |
| *A61B 34/20* | (2016.01) |
| *A61B 8/08* | (2006.01) |
| *A61B 8/00* | (2006.01) |

(Continued)

(52) U.S. Cl.
CPC ........ *A61B 18/1492* (2013.01); *A61B 8/0841* (2013.01); *A61B 8/12* (2013.01); *A61B 8/445* (2013.01); *A61B 8/4494* (2013.01); *A61B 18/1206* (2013.01); *A61B 34/20* (2016.02); *A61B 1/00082* (2013.01); *A61B 2017/00106* (2013.01); *A61B 2017/320069* (2017.08); *A61B 2018/0022* (2013.01); *A61B 2018/00351* (2013.01); *A61B 2018/00577* (2013.01); *A61B 2018/00994* (2013.01); *A61B 2034/2063* (2016.02); *A61B 2090/3784* (2016.02); *A61M 25/10* (2013.01)

(58) Field of Classification Search
CPC ......... A61B 2017/00106; A61B 2017/320069; A61B 2018/0022; A61B 2018/00994; A61B 18/1492; A61B 2034/2063; A61B 1/00082; A61B 8/0841; A61B 8/12; A61B 8/445; A61B 8/4494; A61B 2090/378; A61B 2090/3782; A61B 2090/3784; A61M 25/10
See application file for complete search history.

(56) References Cited

U.S. PATENT DOCUMENTS

| | | |
|---|---|---|
| 5,840,025 A | 11/1998 | Ben-Haim |
| 5,860,974 A | 1/1999 | Abele |

(Continued)

FOREIGN PATENT DOCUMENTS

| | | |
|---|---|---|
| WO | 2005041748 A2 | 5/2005 |
| WO | 2015200518 A1 | 12/2015 |

OTHER PUBLICATIONS

European Search Report dated Oct. 25, 2018.

*Primary Examiner* — Daniel W Fowler
*Assistant Examiner* — Bradford C. Blaise
(74) *Attorney, Agent, or Firm* — Volpe and Koenig, P.C.

(57) ABSTRACT

An inflatable balloon assembly is deployable through the lumen of a probe. The balloon assembly has a plurality of ablation electrodes arranged circumferentially on the balloon about its longitudinal axis, and a plurality of ultrasound transducers circumferentially distributed on the balloon along at least one of its latitudes. The probe is connectable to circuitry configured for powering the ablation electrodes and processing signals from the transducers.

17 Claims, 6 Drawing Sheets

(51) Int. Cl.
 *A61B 18/12* (2006.01)
 *A61B 1/00* (2006.01)
 *A61M 25/10* (2013.01)
 *A61B 90/00* (2016.01)
 *A61B 17/32* (2006.01)
 *A61B 17/00* (2006.01)
 *A61B 18/00* (2006.01)

(56) References Cited

U.S. PATENT DOCUMENTS

| | | |
|---|---|---|
| 6,012,457 A | 1/2000 | Lesh |
| 6,024,740 A | 2/2000 | Lesh et al. |
| 6,117,101 A | 9/2000 | Diederich et al. |
| 6,226,542 B1 | 5/2001 | Reisfeld |
| 6,296,619 B1 | 10/2001 | Brisken et al. |
| 6,301,496 B1 | 10/2001 | Reisfeld |
| 6,814,733 B2 | 11/2004 | Schwartz et al. |
| 6,892,091 B1 | 5/2005 | Ben-Haim et al. |
| 6,997,924 B2 | 2/2006 | Schwartz et al. |
| 7,156,816 B2 | 1/2007 | Schwartz et al. |
| 7,536,218 B2 | 5/2009 | Govari et al. |
| 7,756,576 B2 | 7/2010 | Levin |
| 8,478,383 B2 | 7/2013 | Bar-Tal et al. |
| 8,628,473 B2 | 1/2014 | Sliwa et al. |
| 2002/0019627 A1 | 2/2002 | Maguire et al. |
| 2005/0021015 A1 | 6/2005 | Keidar |
| 2006/0064081 A1 | 3/2006 | Rosinko |
| 2006/0173251 A1 | 8/2006 | Govari et al. |
| 2007/0038078 A1 | 2/2007 | Osadchy |
| 2009/0177090 A1* | 7/2009 | Grunwald ............... A61B 8/02 600/454 |
| 2010/0174189 A1 | 7/2010 | Abraham |
| 2013/0150693 A1* | 6/2013 | D'Angelo ............. A61B 5/036 600/373 |
| 2013/0197363 A1 | 8/2013 | Rankin et al. |
| 2013/0261702 A1 | 10/2013 | Garfield et al. |
| 2014/0121470 A1 | 5/2014 | Scharf et al. |
| 2015/0141982 A1 | 5/2015 | Lee |
| 2016/0016016 A1 | 1/2016 | Taylor et al. |
| 2016/0051321 A1 | 2/2016 | Salahieh et al. |
| 2016/0166310 A1* | 6/2016 | Stewart ............. A61B 18/1206 606/34 |
| 2016/0175041 A1 | 6/2016 | Govari |
| 2016/0183915 A1 | 6/2016 | Govari |
| 2017/0086747 A1 | 3/2017 | Ghaffari et al. |

* cited by examiner

ULTRASOUND TRANSDUCERS ON PREDETERMINED RADII OF BALLOON CATHETER

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to transferring non-mechanical forms of energy to or from the body. More particularly, this invention relates to determining the position of a medical instrument in the body using ultrasound energy to measure a location parameter.

2. Description of the Related Art

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

Circumferential lesions at or near the ostia of the pulmonary veins have been created to treat atrial arrhythmias. U.S. Pat. Nos. 6,012,457 and 6,024,740, both to Lesh, disclose a radially expandable ablation device, which includes a radiofrequency electrode. Using this device, it is proposed to deliver radiofrequency energy to the pulmonary veins in order to establish a circumferential conduction block, thereby electrically isolating the pulmonary veins from the left atrium.

U.S. Pat. No. 6,814,733 to Schwartz et al., which is commonly assigned herewith and herein incorporated by reference, describes a catheter introduction apparatus having a radially expandable helical coil as a radiofrequency emitter. In one application the emitter is introduced percutaneously, and transseptally advanced to the ostium of a pulmonary vein. The emitter is radially expanded, which can be accomplished by inflating an anchoring balloon about which the emitter is wrapped, in order to cause the emitter to make circumferential contact with the inner wall of the pulmonary vein. The coil is energized by a radiofrequency generator, and a circumferential ablation lesion is produced in the myocardial sleeve of the pulmonary vein, which effectively blocks electrical propagation between the pulmonary vein and the left atrium.

Commonly assigned U.S. Patent Application Publication No. 20160175041, entitled Balloon for Ablation around Pulmonary Veins, which is herein incorporated by reference, describes cardiac ablation that is carried out by introducing a catheter into the left atrium, extending a lasso guide through the lumen of the catheter to engage the wall of a pulmonary vein, and deploying a balloon over the lasso guide. The balloon has an electrode assembly disposed its exterior. The electrode assembly includes a plurality of ablation electrodes circumferentially arranged about the longitudinal axis of the catheter. The inflated balloon is positioned against the pulmonary vein ostium, so that the ablation electrodes are in galvanic contact with the pulmonary vein, and electrical energy is conducted through the ablation electrodes to produce a circumferential lesion that circumscribes the pulmonary vein.

Ultrasound transducers have been used to provide information to aid cardiac ablation. For example, U.S. Pat. No. 8,628,473 to Sliva et al. proposes an ablation catheter comprising an ablation element to ablate a biological member at a target region outside the catheter body and one or more acoustic transducers each configured to direct an acoustic beam toward a respective target ablation region and receive reflection echoes therefrom. The distal member includes a transducer housing in which the acoustic transducers are disposed, the transducer housing including at least one transducer window, which is the only portion in the distal member through which the acoustic beam passes. There is at least the at least one transducer window portion of the distal member.

Another example is commonly assigned U.S. Patent Application Publication No. 20160183915, entitled Measurement of Tissue Thickness using Ultrasound and Force Measurements, which is herein incorporated by reference. Wall thickness of a cavity is determined by inserting a catheter into contact with a wall of a cavity in a body of a subject. The distal segment of the catheter is provided with a contact force sensor and an ultrasound transducer. The transducer is actuated to acquire ultrasound reflection data from the wall of the cavity, and while the transducer is actuated, the catheter is reciprocated against the wall of the cavity and the contact force measured between the catheter and the wall of the cavity. The reflection data is correlated with the contact force. A set of the correlated reflection data having the highest correlation with the contact force is identified. The tissue thickness between the inner surface and the identified set of the reflection data is calculated according to the time-of-flight therebetween.

SUMMARY OF THE INVENTION

However, even with catheters that use A-mode ultrasound transducers to find distances from the transducers to the pulmonary vein tissue, there is difficulty in ensuring that a balloon catheter is properly positioned in the pulmonary vein before ablation, and that the ablation electrodes are touching the tissue.

According to disclosed embodiments of the invention, A-mode transducers are distributed along two or more different "latitudes" of the balloon, e.g., 30° and 60° (between the equator and the distal pole of the balloon). Positioning the transducers on different latitudes enables a controller using measurements from the transducers to determine that the balloon is correctly positioned at the entrance to the pulmonary vein. The entrance is effectively a funnel, so that correct positioning of the balloon means that the transducers at, for example, 60° latitude, as well as those at 30° latitude, all give distance readings to the tissue close to zero.

In one embodiment, there are a first set of five ultrasound transducers located on latitude 30°, and a second set of five transducers located on latitude 60°. There are ten ablation electrodes, and the transducers are positioned at the electrodes, and are staggered so as to alternate with one another on different lines of longitude.

There is provided according to embodiments of the invention an apparatus including a probe and an inflatable balloon assembly deployable through the lumen of the probe. The balloon assembly has a plurality of ablation electrodes arranged circumferentially on the balloon about its longitudinal axis, and a plurality of ultrasound transducers circumferentially distributed on the balloon along at least one of its latitudes. The probe is connectable to circuitry configured for powering the ablation electrodes and processing signals from the transducers.

In one aspect of the apparatus a substrate is configured as a plurality of longitudinal strips circumferentially distributed on the balloon and the ablation electrodes are disposed on the strips. The strips and the transducers may be superimposed.

According to a further aspect of the apparatus, the transducers are circumferentially distributed as a first set of transducers at a first latitude and a second set of transducers at a second latitude.

According to a further aspect of the apparatus, there are ten ablation electrodes, and the first set of transducers and the second set of transducers each comprise five transducers.

According to yet another aspect of the apparatus, the first latitude is at 30° above the equator and the second latitude is at 60° above the equator toward the distal pole.

According to yet another aspect of the apparatus, the first latitude is from 20°-40° and the second latitude is from 50°-70° above the equator toward the distal pole.

According to still another aspect of the apparatus, the first set of transducers are staggered with the second set of transducers on respective first and second sets of longitudes.

According to one aspect of the apparatus, the transducers are configured for A-mode operation.

There is further provided according to embodiments of the invention a method, which is carried out by providing a probe, deploying an inflatable balloon through the lumen of the probe beyond its distal portion, arranging a plurality of ablation electrodes circumferentially on the balloon about its longitudinal axis, distributing a plurality of ultrasound transducers circumferentially on the balloon along one of its latitudes, powering the ablation electrodes, and processing signals from the transducers.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.
System Description.

Figure 1:
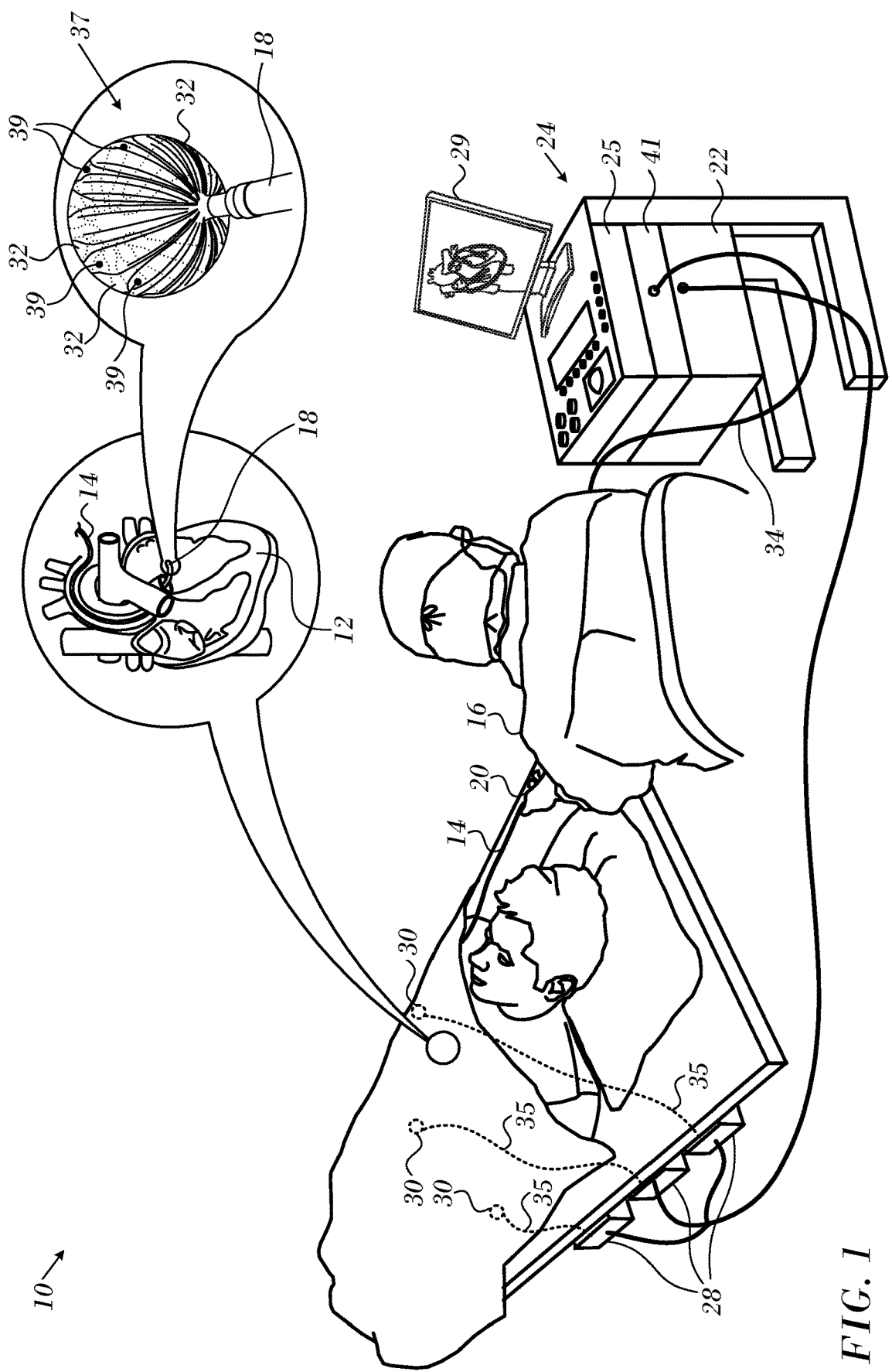
FIG. 1 is a pictorial illustration of a system for performing catheterization procedures on a heart, in accordance with a disclosed embodiment of the invention.

Turning now to the drawings, reference is initially made to FIG. 1, which is a pictorial illustration of a system 10 for performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference.

The system 10 may comprise a general purpose or embedded computer processor, which is programmed with suitable software for carrying out the functions described hereinbelow. Thus, although portions of the system 10 shown in other drawing figures herein are shown as comprising a number of separate functional blocks, these blocks are not necessarily separate physical entities, but rather may represent, for example, different computing tasks or data objects stored in a memory that is accessible to the processor. These tasks may be carried out in software running on a single processor, or on multiple processors. The software may be provided to the processor or processors on tangible non-transitory media, such as CD-ROM or non-volatile memory. Alternatively or additionally, the system 10 may comprise a digital signal processor or hard-wired logic. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically above 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

The distal end of catheter 14 is an expandable balloon 37, having multiple electrodes 32, which are used primarily as ablation electrodes and have known locations on the surface of the balloon, and known relationships to one another. Thus, once the catheter is located in the heart, for example by constructing a current position map, the location of each of the electrodes 32 in the heart is known. One method for generation of a current position map is described in commonly assigned U.S. Pat. No. 8,478,383 to Bar-Tal et al., which is herein incorporated by reference. Ultrasound transducers 39 positioned on the balloon 37 operate in A-mode to determine respective distances from target tissue, as described below. The console 24 typically includes an ultrasound processor 41 to interpret signals from the transducers 39.

In addition to conducting radiofrequency current through the electrodes 32, other electrical signals can be conveyed to and from the heart 12 from the electrodes 32 via cable 34 to the console 24. Pacing signals and other control signals may be conveyed from the console 24 through the cable 34 and the electrodes 32 to the heart 12.

Wire connections 35 link the console 24 with body surface electrodes 30 and other components of a positioning sub-system for measuring location and orientation coordinates of the catheter 14. The processor 22, or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted near the distal tip 18 of the catheter 14.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. A suitable positioning subsystem is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes as described in further detail below.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally applied reference patch attached to the exterior of the subject's body, or on an internally-placed catheter, which is inserted into the heart 12 and maintained in a fixed position relative to the heart 12. The system 10 may receive image data from an external imaging modality, such as an MRI unit or the like and includes image processors that can be incorporated in or invoked by the processor 22 for generating and displaying images that are described below.

Figure 2:
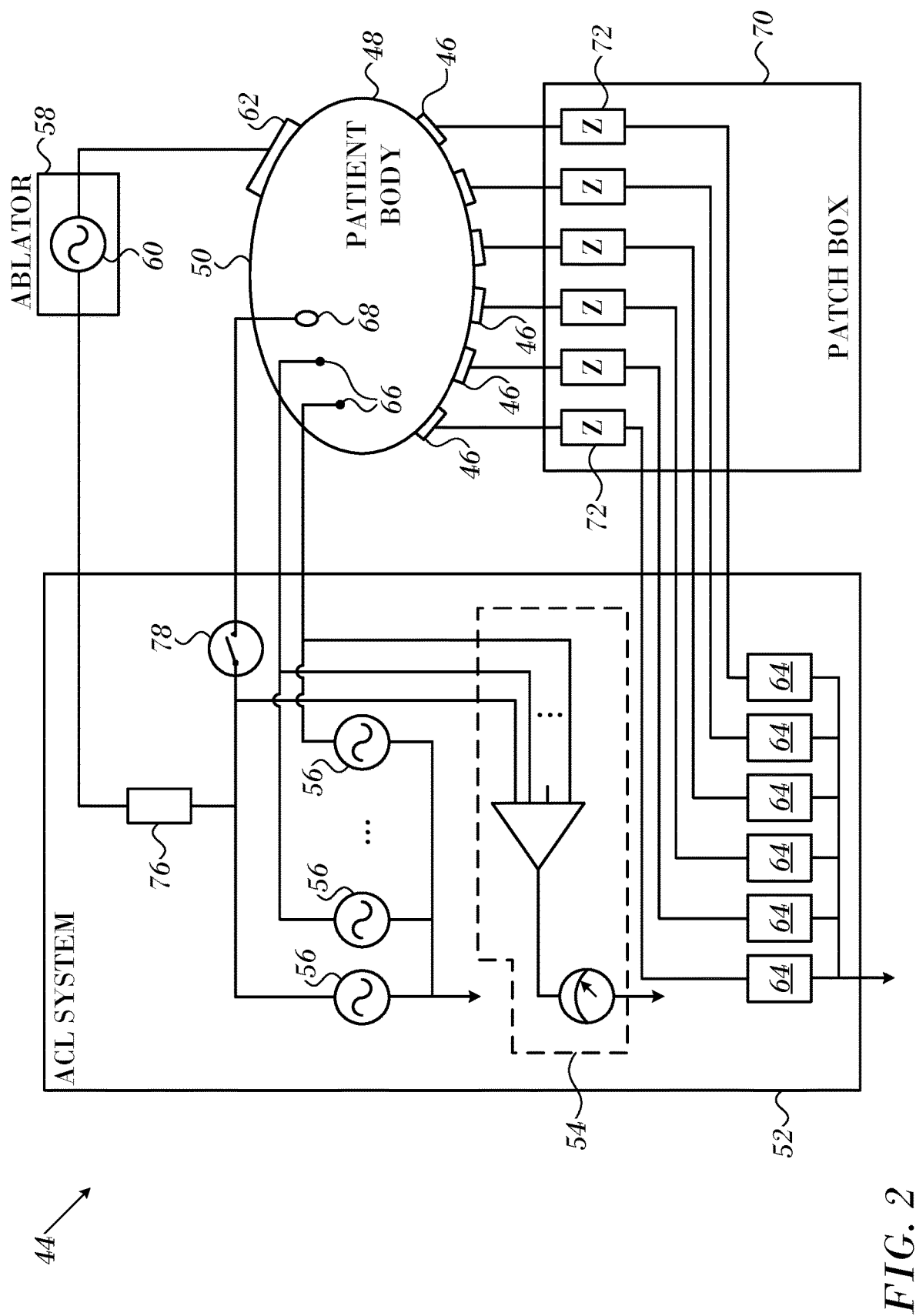
FIG. 2 is a schematic diagram of an ablation and active current location (ACL) circuit for use with the system shown in FIG. 1.

Reference is now made to FIG. 2, which is a schematic diagram of an ablation and active current location (ACL) circuit 44 for use with the system shown in FIG. 1. This arrangement is similar to that described in U.S. Patent Application Publications 2006/0173251, to Govari et al., and 2007/0038078, to Osadchy, which are herein incorporated by reference. The arrangement can be modified to operate in accordance with the principles of the present invention. A brief description follows for convenience of presentation.

A plurality of body surface electrodes 46, which can be adhesive skin patches, are coupled to a body surface 48 (e.g., the skin) of subject 50. The body surface electrodes 46 are sometimes referred to herein as "patches". In cardiac applications the body surface electrodes 46 are usually distributed so as to surround the heart, three on the chest of the subject and three on the back. However, the number of the body surface electrodes 46 is not critical, and they may be placed at convenient locations on the body surface 48 in the general vicinity of the site of the medical procedure.

A control unit 52, normally disposed in the console 24 (FIG. 1), includes current measurement circuitry 54 and one or more catheter electrode transmitters 56 for driving a current through one or more of the electrodes 46 to one or more of the body surface electrodes 46 at respective working frequencies. The control unit 52 is linked to the positioning processor 22 (FIG. 1). The control unit 52 is linked to an ablator 58, which comprises at least one ablation generator 60. Currents through the body surface electrodes 46 and an ablator body surface electrode 62 flow in a circuit with the ablation generator 60 and are measured by respective current measurement circuits that are disposed within body electrode receivers 64, sometimes referred to herein as "patch measurement circuits". The body electrode receivers 64 are typically incorporated in the control unit 52. Alternatively, they may be affixed to the body surface electrodes 46. Catheter electrodes are represented in FIG. 2 as measurement electrodes 66 (circles) and a dual-purpose electrode 68

(ellipse). The dual-purpose electrode 68 functions as an ablation electrode and also serves as one of the measurement electrodes.

The body surface electrodes 46 are connected to the body electrode receivers 64 via a patch box 70, which protects the system from ablation and defibrillation currents. Typically the system is configured with six body electrode receivers 64. The patch box parasitic impedances 72 (Z), are measured during production and thus known a priori. These impedances are discussed below.

Typically, although only two measurement electrodes 66 are shown for convenience, about 80 measurement electrodes are used for impedance measurements. Typically there are one or two ablation electrodes. The coordinates of a catheter inside the body are determined by passing currents between electrodes on the catheter and the body surface electrodes 46.

The control unit 52 may also control an ablation circuit, comprising ablator 58, and the dual-purpose electrode 68. The ablator 58 is typically disposed externally to the control unit 52 and incorporates the ablation generator 60. It connects with the ablator body surface electrode 62 and to an ablator filter 76, which in this example is shown within the control unit 52. However this location is not essential. A switch 78 configures the ablator circuit for different modes of operation as described below. It will be noted from inspection of FIG. 2 that the ablation circuit is connected to one of the catheter electrode transmitters 56.

Figure 3:
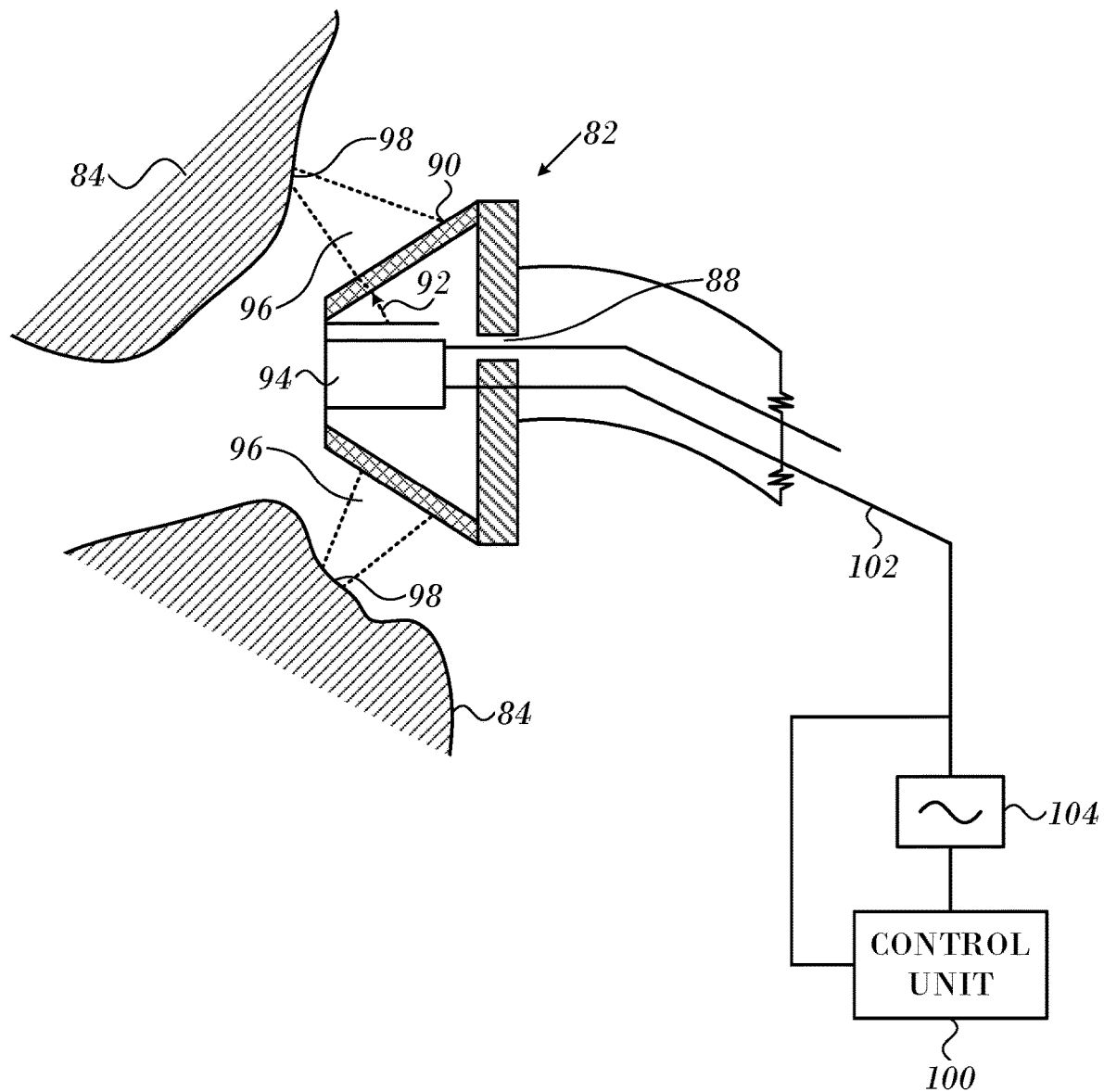
FIG. 3 is a sectional schematic view of a transducer assembly in an operational position in accordance with an embodiment of the invention.

Reference is now made to FIG. 3, which is a sectional schematic view of a transducer assembly 82 in an operational position at a pulmonary vein ostium 84 in accordance with a preferred embodiment of the invention. Transducer assembly 82 is disposed proximate the ostium 84, external to an optional anchoring balloon (not shown). The use of ultrasonic beam focusing techniques eliminates the difficulty of physically conforming the transducer to the wall of the pulmonary vein, as is required by conventional techniques, which often required multiple versions of the catheter, each dimensioned to one of many anatomic variations of the structures near the target ablation zone.

The transducer assembly 82 has a lumen 88. A body section 90 is preferably shaped as a truncated cone, preferably having an inclination angle 92 of approximately 20 degrees. Thus, the cross section of a proximal portion of the body section 90 is larger than the cross section of its distal portion. A piezoelectric element 94 of known type, such as a ceramic, is present within the body section 90. The transducer assembly 82 functions as an omnidirectional ultrasonic lens, forming a generally forward-directed circumferential beam 96, indicated by dashed lines. The beam 96 converges onto target tissue 98. The piezoelectric element 94 may be realized as an array of transducers, which can be tuned, under control of a control unit 100, so as to shape the beam 96 as may be required for a particular ablation procedure, in order to adapt the beam to the local anatomy. This can be done in a known manner, for example by operating elements of the array out of phase with one another.

The transducer assembly 82 is connected by a cable 102 to a suitable power source 104 and to the control unit 100 and can be operated in A-mode. Preferably the transducer assembly 82 is 4.0 mm in length, and has an OD of 2.6 mm. The transducer assembly 82 is quarter-wave impedance matched, using air-backing material within the body section 90. It preferably operates at an excitation frequency of 3-4 MHz, and has a focal depth of 15 mm. Typical driving power is 30-40 W. Structures suitable for the components of the transducer assembly 82 are disclosed, for example, in U.S. Pat. No. 6,296,619, and the above-noted U.S. Pat. No. 6,117,101, which are incorporated herein by reference. It is also possible to construct the transducer assembly 82 as a thin-film polymer wrapped about the outer surface of the catheter. The active sites to be ablated may be identified using the location and mapping system disclosed in commonly assigned U.S. Pat. No. 5,840,025, which is herein incorporated by reference.

Balloon Catheter.

Figure 4:
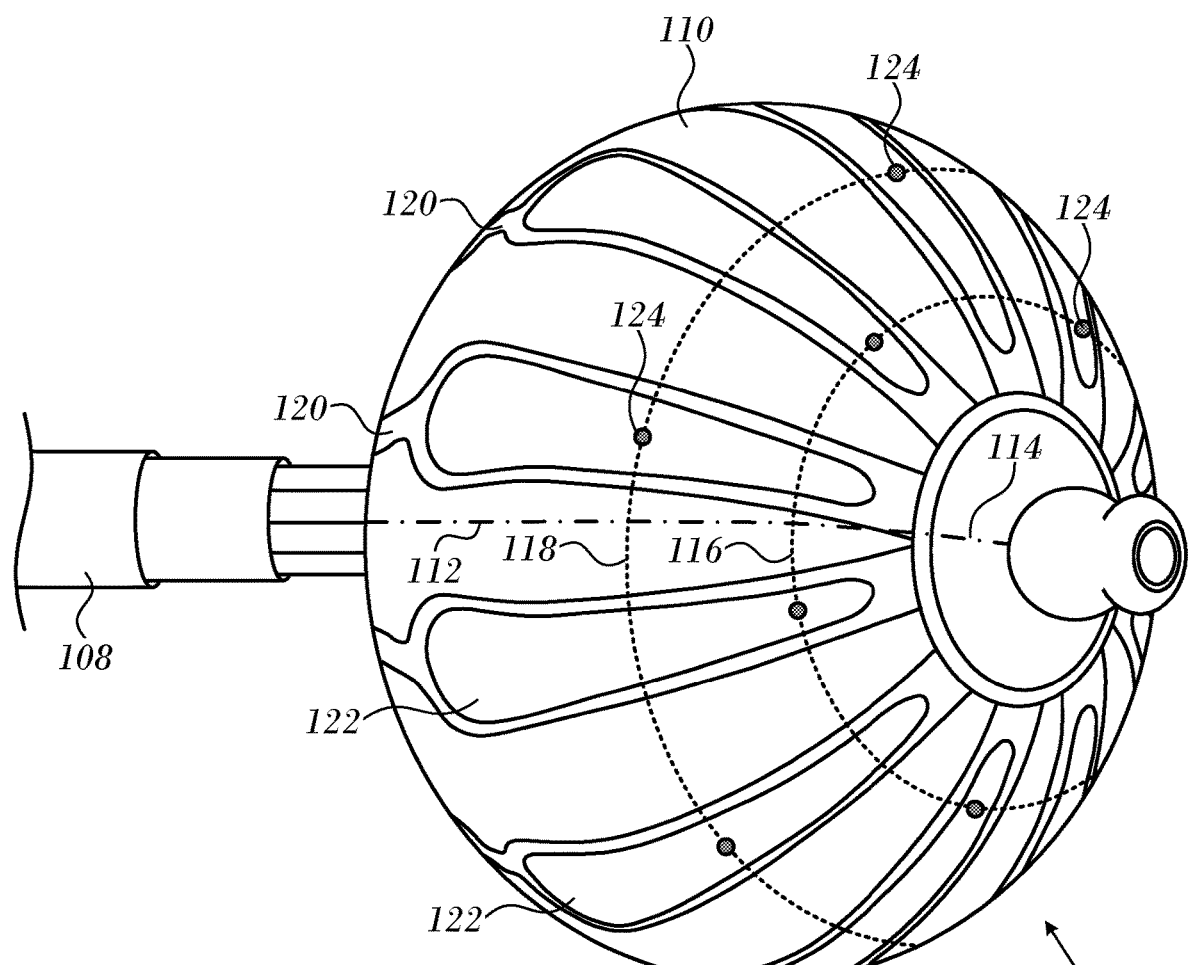
FIG. 4 is an oblique elevation of a balloon assembly at the distal end of a catheter shaft in accordance with an embodiment of the invention.

Reference is now made to FIG. 4, which is an oblique elevation of a balloon assembly 106 at the distal end of a catheter shaft 108 in accordance with an embodiment of the invention. The balloon assembly 106 includes an expanded balloon 110, which typically is in the form of a sphere or an oblate sphere, in which a diameter 112 through a distal pole 114, coaxial with a longitudinal axis of the shaft, is less than an equatorial diameter (not shown) that is perpendicular to the diameter 112. Parallel lines of latitudes are shown at 60° (latitude 116) and 30° (latitude 118) measured from the equator of the balloon 110 toward the distal pole 114. A variation of ±10° may be tolerated in the latitudes, so that in different embodiments the latitudes could vary from 50°-70° and 20°-40°, respectively. Situated on the surface wall of the balloon 110 are multiple longitudinal substrate strips 120 made of polyimide upon which ablation electrodes 122 are formed. In the example of FIG. 4 there are 10 electrodes 122 distributed about the circumference of the balloon 110. The electrodes 122 and transducers 124 may be incorporated into the balloon 110 in different ways, for example, by adhering with an adhesive, stamping, printing, wire bonding, soldering, or combinations thereof, as known in the art. Flexible circuitry may be employed.

The expanded balloon 110 is deployable through a lumen in the shaft 108. The balloon 110 is configured to engage and ablate the wall of a pulmonary vein in order to correct aberrant conduction, as described, for example in commonly assigned U.S. Pat. No. 6,997,924 and U.S. Patent Application Publication No. 20160175041, which are herein incorporated by reference. Multiple A-mode ultrasound transducers 124 are distributed on the balloon 110 It has been found that a near-optimal arrangement of the transducers 124 is a circumferential distribution of one set of the transducers 124 at 60° latitude 116 and another set at 30° latitude 118. Because the pulmonary veins taper from widest diameters at their ostia, when the balloon 110 is navigated and expanded within the pulmonary vein, as described, for example in the above noted U.S. Patent Application Publication No. 20160175041, its surface closely approximates the pulmonary vein intima both at 60° latitude 116, where the diameter of the pulmonary vein is relatively small and at 30° latitude 118, where it is relatively large. The signals from the transducers 124 correspond to a distance between the transducers 124 and the wall of the pulmonary vein of nearly zero.

In the embodiment of FIG. 4, there are a total of 10 transducers 124: five each in the sets at 60° latitude 116 and 30° latitude 118. The two sets are staggered with respect to one another so as to lie on alternate lines of longitude. Each set is equally distributed around the circumference of the balloon 110. Preferably the sets of transducers 124 are associated with respective sets of strips 120 as shown in FIG. 4, wherein the transducers 124 and the strips 120 are superimposed. The transducers 124 may be superimposed on the electrodes 122.

The number and configuration of the electrodes 122 and transducers 124 may be varied as required for a particular medical application and the geometry of the vessel being ablated. While the embodiment of FIG. 4 is suitable for most pulmonary veins, the latitudes for the transducers 124 may be chosen such that the contact zones between the balloon and the intima match a particular taper of the target vessel.

Figure 5:
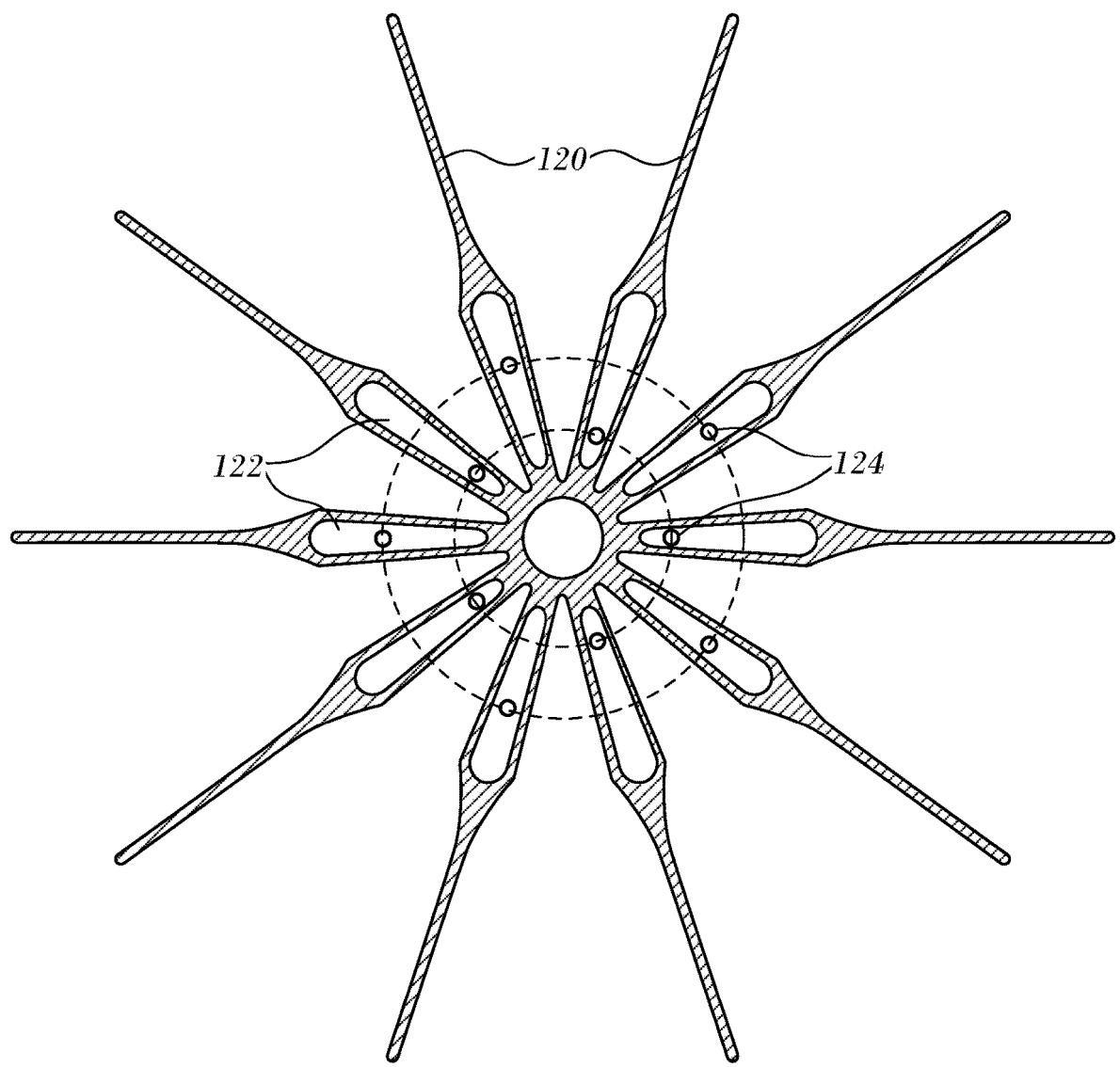
FIG. 5 is a projection of a portion of the balloon assembly shown in FIG. 4 in accordance with an embodiment of the invention.

Reference is now made to FIG. 5, which is a projection of a portion of the balloon assembly 106 (FIG. 4) showing the layout of the strips 120 in relation to the electrodes 122, and the sets of transducers 124 on two concentric circles representing lines of latitude in accordance with an embodiment of the invention.

Figure 6:
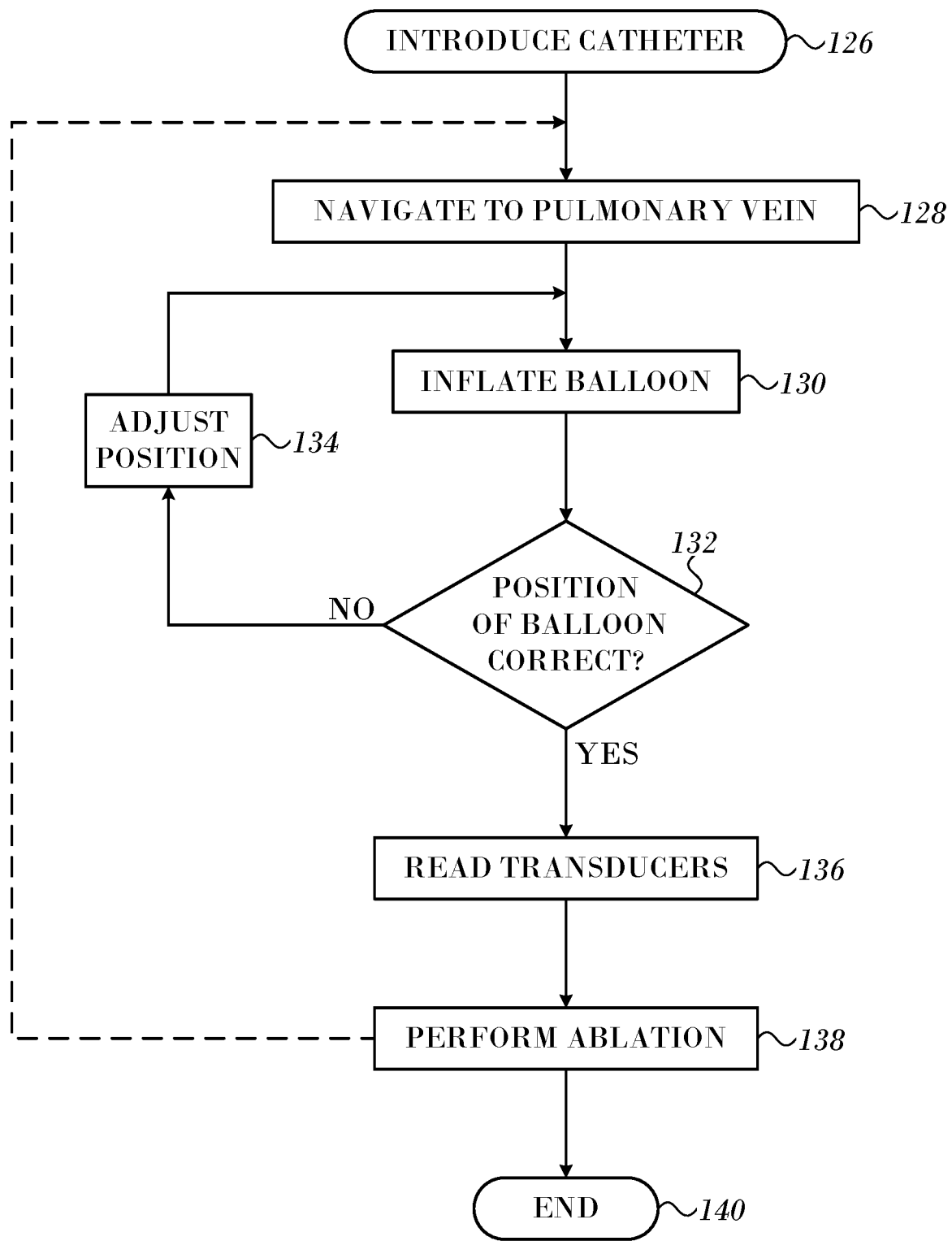
FIG. 6 is a flow chart illustrating a method of cardiac catheterization and pulmonary vein isolation in accordance with an embodiment of the invention.

Reference is now made to FIG. 6, which is a flow chart illustrating a method of cardiac catheterization and pulmonary vein isolation in accordance with an embodiment of the invention.

At initial step 126 a cardiac balloon catheter configured as described above in FIG. 1 and FIG. 4 is conventionally introduced into the left atrium of a heart.

Next, at step 128 the balloon is navigated to engage the interior wall of a pulmonary vein. This may be done using a guide, such as the lasso guide described in the above-noted U.S. Patent Application Publication No. 20160175041. When a guide is used, the balloon may be extended over the guide into an operating position.

Next, at step 130 the balloon is inflated. Optionally, a radio-opaque contrast agent may then be injected through the lumen of the catheter in order to confirm that the balloon is in a correct position against the pulmonary vein ostium.

Control now proceeds to decision step 132, where it is determined if the balloon is correctly positioned. This is the case when the distance readings from at least one set of transducers obtained in step 130 are essentially zero. If the determination at decision step 132 is negative, then control proceeds to step 134. The balloon is repositioned, which can include being partially or fully deflated during the repositioning process. Control returns to step 130 to iterate the placement until the position is determined to be correct.

If the determination at decision step 132 is affirmative, then control proceeds to step 136. A-mode readings are taken from the ultrasound transducers on the balloon to determine the respective distances between the transducers and the inner wall of the pulmonary vein.

Next, at step 138, ablation is performed, e.g., using the electrodes 122 of the electrode of the balloon assembly 106 (FIG. 4). Typically, a circumferential lesion is created in a region of tissue that circumscribes the pulmonary vein. The lesion blocks electrical propagation and effectively electrically isolates the pulmonary vein from the heart. Post-ablation electrograms may be obtained in order to confirm functional isolation of the pulmonary vein.

After completion of the ablation, the procedure may be iterated using another pulmonary vein ostium by withdrawal of the balloon. Control may then return to step 128. Alternatively, the procedure may end by removal of the catheter at final step 140.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. An apparatus comprising:
a probe having a distal portion and a lumen;
an inflatable balloon having a surface wall, a longitudinal axis and latitudes between an equator and a distal pole on the surface wall;
a plurality of ablation electrodes arranged circumferentially on the balloon about the longitudinal axis; and
a first plurality of ultrasound transducers circumferentially distributed on the balloon along a first one of the latitudes and superimposed on a first set of ablation electrodes of the plurality of ablation electrodes such that a sole ultrasound transducer of the first plurality of ultrasound transducers is superimposed on each ablation electrode of the first set of ablation electrodes, each of the first set of ablation electrodes spanning the first one of the latitudes and a second one of the latitudes;
a second plurality of ultrasound transducers circumferentially distributed on the balloon along the second one of the latitudes and superimposed on a second set of ablation electrodes of the plurality of ablation electrodes such that a sole ultrasound transducer of the second plurality of ultrasound transducers is superimposed on each ablation electrode of the second set of ablation electrodes, each of the second set of ablation electrodes spanning the first one of the latitudes and the second one of the latitudes, wherein the first plurality of ultrasound transducers are staggered with the second plurality of ultrasound transducers on respective first and second sets of longitudes.

2. The apparatus according to claim 1, further comprising a substrate configured as a plurality of longitudinal strips circumferentially distributed on the balloon wherein the plurality of ablation electrodes are disposed on the strips.

3. The apparatus according to claim 2, wherein the strips and the first and second plurality of ultrasound transducers are superimposed.

4. The apparatus according to claim 1, wherein the first plurality of ultrasound transducers and the second plurality of ultrasound transducers each comprise five ultrasound transducers.

5. The apparatus according to claim 1, wherein the first one of the latitudes is at least 30° above the equator and the second one of the latitudes is at least 60° above the equator toward the distal pole.

6. The apparatus according to claim 1, wherein the first one of the latitudes is from 20°-40° and the second one of the latitudes is at least 60° above the equator toward the distal pole.

7. The apparatus according to claim 1, wherein the first and second plurality of ultrasound transducers are configured for A-mode operation.

8. A method comprising:
providing a probe having a distal portion and a lumen;
deploying an inflatable balloon through the lumen beyond the distal portion, the balloon having a surface wall, a longitudinal axis and latitudes between an equator and a distal pole on the surface wall;
arranging a plurality of ablation electrodes circumferentially on the balloon about the longitudinal axis;
arranging a first set of ultrasound transducers circumferentially on the balloon along a first latitude and superimposed on a first set of ablation electrodes of the plurality of ablation electrodes such that a sole ultrasound transducer of the first set of ultrasound transducers is superimposed on each ablation electrode of the first set of ablation electrodes, each of the first set of ablation electrodes spanning the first latitude and a second latitude and distributing a second set of ultrasound transducers circumferentially on the balloon along the second latitude and superimposed on a second set of ablation electrodes of the plurality of ablation electrodes such that a sole ultrasound transducer of the second set of ultrasound transducers is superimposed on each ablation electrode of the second set of ablation electrodes, each of the second set of ablation electrodes spanning the first latitude and the second latitude, wherein the first set of ultrasound transducers are staggered with the second set of ultrasound transducers on respective first and second sets of longitudes;

processing signals from the first set of ultrasound transducers and the second set of ultrasound transducers;

determining that the inflatable balloon is at an ablation position based on the signals from both of the first set of ultrasound transducers and the second set of ultrasound transducers; and powering the plurality of ablation electrodes based on the determination.

9. The method according to claim 8, further comprising:
circumferentially distributing a substrate configured as a plurality of longitudinal strips on the balloon; and
disposing the plurality of ablation electrodes on the strips.

10. The method according to claim 9, further comprising superimposing the strips and the first and second set of ultrasound transducers.

11. The method according to claim 8, further comprising superimposing the plurality of ablation electrodes and the first and second set of ultrasound transducers.

12. The method according to claim 8, wherein the plurality of ablation electrodes comprise ten ablation electrodes, and the first set of ultrasound transducers and the second set of ultrasound transducers each comprise five ultrasound transducers.

13. The method according to claim 8, wherein the first latitude is at least 30° above the equator and the second latitude is at least 60° above the equator toward the distal pole.

14. The method according to claim 8, wherein the first latitude is from 20°-40° and the second latitude is from 50°-70° above the equator toward the distal pole.

15. The method according to claim 8, further comprising operating the first set of ultrasound transducers in A-mode.

16. A system comprising:
a probe having a distal portion and a lumen;
an inflatable balloon having a surface wall, a longitudinal axis and latitudes between equator and a distal pole on the surface wall;
a plurality of ablation electrodes arranged circumferentially on the balloon about the longitudinal axis;
a first plurality of ultrasound transducers circumferentially distributed on the balloon along a first one of the latitudes and superimposed on a first set of ablation electrodes of the plurality of ablation electrodes, such that a sole ultrasound transducer of the first plurality of ultrasound transducers is superimposed on each ablation electrode of the first set of ablation electrodes, each of the first set of ablation electrodes spanning the first one of the latitudes and a second one of the latitudes;
a second plurality of ultrasound transducers circumferentially distributed on the balloon along the second one of the latitudes and superimposed on a second set of ablation electrodes of the plurality of ablation electrodes, such that a sole ultrasound transducer of the second plurality of ultrasound transducers is superimposed on each ablation electrode of the second set of ablation electrodes, each of the second set of ablation electrodes spanning the first one of the latitudes and the second one of the latitudes; and
a processor configured to receive first signals from the first plurality of ultrasound transducers and determine that a distance between the inflatable balloon and a tissue is approximately zero based on the first signals.

17. The system of claim 16, wherein the processor is further configured to receive second signals from the second plurality of ultrasounds transducers and determine that the distance between the inflatable balloon and a tissue is approximately zero based on the first signals and the second signals.

* * * * *

UNITED STATES PATENT AND TRADEMARK OFFICE
CERTIFICATE OF CORRECTION

| | | |
|---|---|---|
| PATENT NO. | : 10,751,121 B2 | |
| APPLICATION NO. | : 15/637191 | |
| DATED | : August 25, 2020 | |
| INVENTOR(S) | : Assaf Govari et al. | |

It is certified that error appears in the above-identified patent and that said Letters Patent is hereby corrected as shown below:

In the Specification
In Column 1, Line 65, delete "20160175041," and insert -- 2016/0175041, --, therefor.
In Column 2, Line 28, delete "20160183915," and insert -- 2016/0183915, --, therefor.
In Column 8, Line 39, delete "20160175041," and insert -- 2016/0175041, --, therefor.
In Column 8, Line 49, delete "20160175041," and insert -- 2016/0175041, --, therefor.
In Column 9, Line 24, delete "20160175041." and insert -- 2016/0175041. --, therefor.

In the Claims
In Column 10, Line 5, in Claim 1, delete "an_equator" and insert -- an equator --, therefor.

Signed and Sealed this
Sixth Day of December, 2022

Katherine Kelly Vidal
*Director of the United States Patent and Trademark Office*